United States Patent

Urella et al.

[11] Patent Number: 5,821,468
[45] Date of Patent: Oct. 13, 1998

[54] LAMINATED NAP COMFORT COVER FOR EAR SEAL

[75] Inventors: Richard M. Urella, Charlton; Robert E. Dalbec, Worcester; Domenic L. Fratantonio, Shrewsbury, all of Mass.

[73] Assignee: David Clark Company, Inc., Worcester, Mass.

[21] Appl. No.: 650,763

[22] Filed: May 20, 1996

[51] Int. Cl.⁶ .............................. H04R 25/00; A42B 1/06

[52] U.S. Cl. .............................................. 181/129; 2/209

[58] Field of Search ............................ 181/129; 381/183, 381/188, 205; 2/209

[56] References Cited

U.S. PATENT DOCUMENTS

| | | | |
|---|---|---|---|
| 4,572,323 | 2/1986 | Randall | 181/129 |
| 4,572,324 | 2/1986 | Fidi et al. | 181/129 |
| 4,856,118 | 8/1989 | Sapiejewski | 2/209 |
| 4,905,322 | 3/1990 | Aileo et al. | 2/209 |
| 5,138,722 | 8/1992 | Urella et al. | |
| 5,148,887 | 9/1992 | Murphy | 181/129 |

*Primary Examiner*—Khanh Dang
*Attorney, Agent, or Firm*—Samuels, Gauthier, Stevens & Reppert

[57] ABSTRACT

An ear seal for an ear cup in a noise attenuating headset. The ear seal surrounds an opening communicating with the interior of the earcup. The ear seal includes a continuous conformable element surrounding the opening and a fabric cover surrounding the opening. The cover overlays and is heat sealed to the element.

5 Claims, 1 Drawing Sheet

LAMINATED NAP COMFORT COVER FOR EAR SEAL

BACKGROUND OF THE INVENTION

1. Field of the Invention

This invention relates to a seal assembly for use on the earcups of a noise attenuating headset. The ear seal assembly is configured and structured to improve comfort without adversely affecting noise attenuation.

2. Background of the Invention

Noise attenuating headsets employ circumaural earcups which typically comprise plastic domes. Conformable ear seals are interposed between the earcups and the wearer's head to assist in isolating the ears from offending noise originating outside the earcups. The earcups are typically attached to a resilient suspension assembly which applies a force urging the ear seals in place against the head of the wearer.

Typically the seal assemblies consist of polymeric materials. When placed against the wearer's head, the polymeric material is uncomfortable, especially in the hot weather when a person is perspiring. A prior art method employed to add to the wearer's comfort includes overlying the seal and the opening surrounded by the seal with a cloth covering. Hence, the covering rather than the polymeric material rests against the wearer's head. While this design improved comfort, it was at the expense of noise attenuation. Because the cloth covering occluded the opening surrounded by the seal, the wearer's ear could not fully be received in the ear cup, thus preventing the ear seal from tightly contacting the wearer's head.

A primary objective of the present invention is to cover the head-contacting portions of an ear seal with a fabric, without occluding the opening surrounded by the ear seal, and without adversely affecting the noise attenuating capabilities of the ear seal.

A further objective is to provide an improved and more efficient method of making an ear seal having fabric on the head-contacting portions thereof.

These and other objectives and advantages of the present invention will become more apparent as the description proceeds with reference to the accompanying drawings.

SUMMARY OF THE INVENTION

According to one aspect of the present invention, there is provided a seal assembly for use on the earcups of a noise attenuating headset. Improved comfort is realized by laminating a fabric ring to the head-contacting portions of the ear seal. The fabric ring rests against the wearer's head and thus serves to better absorb and dissipate moisture, e.g., perspiration under humid and/or elevated temperature conditions.

According to another aspect of the present invention, the fabric ring is integrally associated with an underlying polyurethane backing, the latter serving as a melt bondable adhesive which attaches the fabric ring to the ear seal during the vacuum forming operation.

DETAILED DESCRIPTION OF THE PREFERRED EMBODIMENTS

Figure 1:
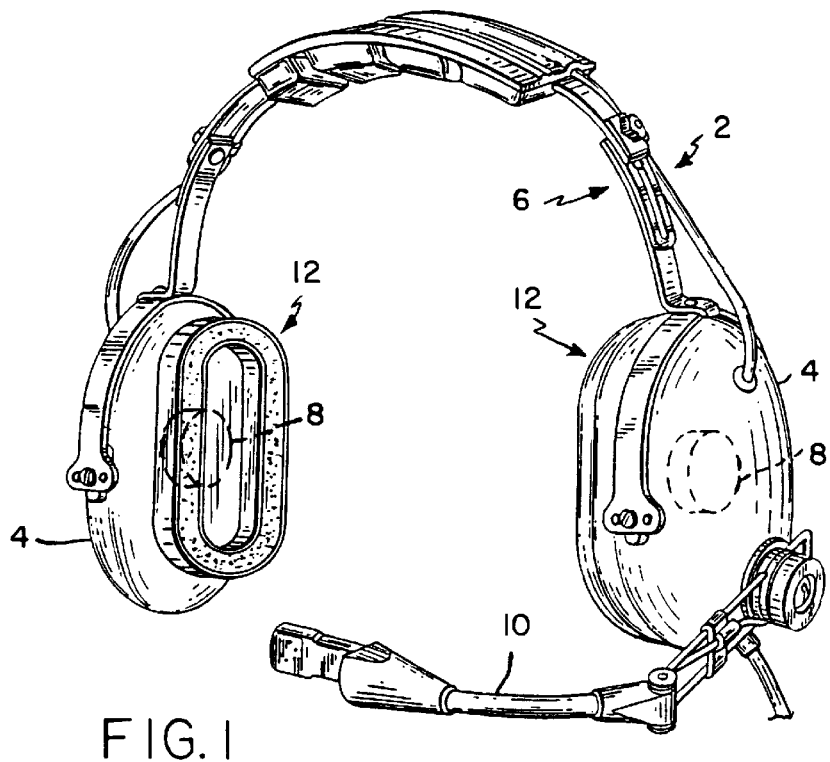
FIG. 1 is a perspective view of a headset in accordance with the present invention.

FIG. 1 illustrates a noise attenuating headset 2 in accordance with the present invention. The headset includes earcups 4 which are attached to a spring and suspension assembly 6. Speakers 8 and microphone boom assembly 10 are provided for communication capabilities. Each of the earcups further include earseals 12 which are attached in a known manner to inwardly facing rims of the earcups 4.

Figure 2:
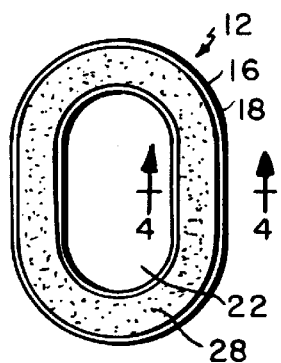
FIG. 2 is a top plan view of a seal assembly in accordance with the present invention.
Figure 3:
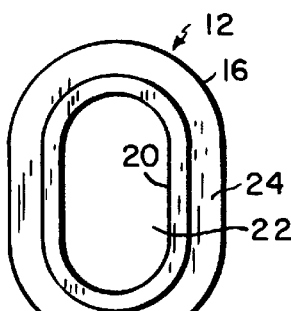
FIG. 3 is a bottom plan view of a seal assembly in accordance with the present invention.
Figure 4:
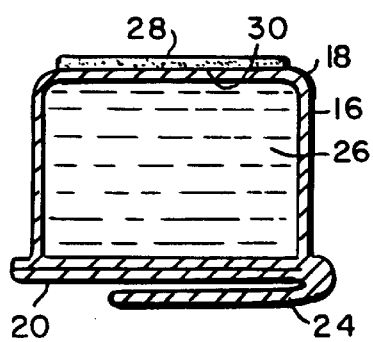
FIG. 4 is an enlarged cross-section view of a seal assembly in accordance with the present invention taken along line 4—4 of FIG. 2.

With additional reference to FIGS. 2–4, it will be seen that the seal assembly 12 of the present invention includes a thin flexible ring-shaped sheath 16 having an upper portion 18 and a lower or bottom portion 20. The sheath 16 is typically formed from polyurethane or the like, and surrounds an opening 22 through which sound passes from the speaker 8 contained with the earcup 4 to the ear of the wearer. The bottom portion 20 is formed integrally with a concentric ring-shaped flap portion 24. The flap portion 24 provides a means of attaching the seal assembly 12 to the earcup 4. Conventional earcups typically include rims configured to coact in interengagement with the flap portions 24. A conformable noise attenuating material 26, for example, a mixture of dilatant silicone compound and a silicone oil, is enclosed within the sheath 16.

Figure 6:
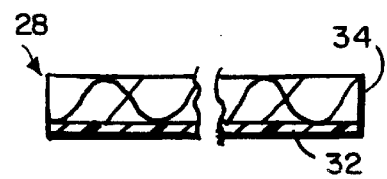
FIG. 6 is an enlarged cross-section view of a laminated composite in accordance with the present invention taken along line 6—6 of FIG. 5.

A fabric or specifically a laminated composite ring 28, preferably a polyester nap or the like, is laminated to the top surface 30 of the ear seal 12. The laminated composite may, for example, be that supplied by Mann Industries, Inc. under the product designation 13313P-01HA000. The laminated composite 28 is configured and dimensioned to overlay the ring-shaped sheath 16, and comprises a polyester material 32 and a clear polyurethane backing 34 as illustrated in FIG. 6.

Figure 5:
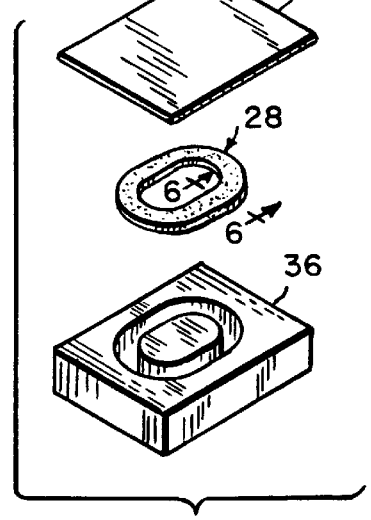
FIG. 5 is an exploded perspective view of two components of the seal assembly prior to assembly and prior to forming.

Referring to FIG. 5, a vacuum form mold 36 is used to heat seal the laminated composite 28 to the polyurethane sheath 16. First a ring-shaped piece of laminated composite 28, is placed in the mold 36 with the urethane side 34 facing up. Next a sheet of polyurethane, i.e. the sheath material 16, is placed in the mold 36 on top of the laminated composite 28. The polyurethane is vacuum formed under increased pressure and temperature in the mold 36 causing a heat seal between the polyurethane sheet 16 and the urethane surface of the laminated composite. The thus formed sheet 16 and its integrally attached composite 28 is then assembled in a conventional manner as part of the ear seal 12.

The polyester nap material 30 is thus integrally applied in an efficient cost effective manner, and once in place, contributes significantly to overall comfort without in any way disrupting or lessening the noise attenuating capabilities of the ear seal.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described the invention, what is now claimed is:

1. An ear seal for an ear cup in a noise attenuating headset, said ear seal surrounding an opening communicating with the interior of said earcup, said ear seal comprising:

a continuous conformable element surrounding said opening, said element including an outer layer enveloping noise attenuating material; and a fabric cover, said cover overlaying and being heat sealed to said element.

2. The ear seal of claim 1, wherein said outer layer is comprised of a polyurethane sheet.

3. The ear seal of claim 1, wherein said fabric cover is a laminated composite consisting of polyester nap and a urethane.

4. The ear seal of claim 1, wherein said ear seal is in the shape of an annular ring.

5. The ear seal of claim 1, wherein said fabric cover is in the shape of an annular ring.

* * * * *